United States Patent
Walls (10) Patent No.: US 7,742,807 B1
(45) Date of Patent: Jun. 22, 2010

(54) MUSICAL REPRESENTATION OF CARDIAC MARKERS

(75) Inventor: George Walls, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 657 days.

(21) Appl. No.: 11/557,424

(22) Filed: Nov. 7, 2006

(51) Int. Cl.
*A61B 5/04* (2006.01)

(52) U.S. Cl. ...................................... 600/509

(58) Field of Classification Search ............. 607/30–32, 607/59–60; 128/899; 482/3; 600/301, 323, 600/365, 509
See application file for complete search history.

(56) References Cited

U.S. PATENT DOCUMENTS

| | | |
|---|---|---|
| 4,791,936 A | 12/1988 | Snell et al. |
| 5,716,382 A | 2/1998 | Snell |
| 5,891,180 A | 4/1999 | Greeninger et al. |
| 5,954,666 A | 9/1999 | Snell |
| 5,974,341 A | 10/1999 | Er et al. |
| 6,044,301 A | 3/2000 | Hartlaub et al. |
| 6,067,473 A | 5/2000 | Greeninger et al. |
| 6,070,102 A | 5/2000 | Hartlaub et al. |
| 6,082,367 A | 7/2000 | Greeninger et al. |
| 6,216,038 B1 | 4/2001 | Hartlaub et al. |
| 6,247,474 B1 | 6/2001 | Greeninger et al. |
| 6,370,433 B1 | 4/2002 | Hartlaub et al. |
| 6,450,172 B1 * | 9/2002 | Hartlaub et al. ............. 128/899 |
| 6,512,953 B2 | 1/2003 | Florio et al. |
| 6,748,274 B2 | 6/2004 | Levine et al. |
| 6,928,321 B1 | 8/2005 | Kroll |
| 2003/0050566 A1 | 3/2003 | Ujhelyi et al. |
| 2005/0010120 A1 | 1/2005 | Jung et al. |
| 2005/0027182 A1 * | 2/2005 | Siddiqui et al. ............. 600/365 |
| 2006/0167365 A1 | 7/2006 | Bharmi |
| 2006/0167518 A1 | 7/2006 | Gill et al. |
| 2006/0167519 A1 | 7/2006 | Gill et al. |

FOREIGN PATENT DOCUMENTS

| | | |
|---|---|---|
| EP | 1075310 B1 | 2/2001 |
| EP | 1075311 B1 | 2/2001 |
| EP | 1075312 B1 | 2/2001 |
| WO | WO99/55418 | 11/1999 |
| WO | WO99/55419 | 11/1999 |

\* cited by examiner

*Primary Examiner*—George Manuel
*Assistant Examiner*—Robert N Wieland (57) ABSTRACT

Cardiac electrical activity includes intrinsic signals as well as paced or stimulated signals. Waveforms of cardiac electrical activity may be detected by a variety of systems, including surface ECG systems and various implantable cardiac devices including implantable cardiac stimulation devices. Intrinsic cardiac signals and various cardiac conditions influence these waveforms in ways that can be identified using various detection criteria, and from which cardiac markers may be generated. Musical notations are linked to these cardiac markers as appropriate, and are sounded as a function of time to generate musical sound which is indicative of the patient's cardiac function.

16 Claims, 9 Drawing Sheets

MUSICAL REPRESENTATION OF CARDIAC MARKERS

FIELD OF THE INVENTION

The present invention relates to cardiac health, and more particularly to the musical representation of cardiac markers.

DESCRIPTION OF THE RELATED ART

The process of screening, diagnosing and treating cardiovascular disease, including assessing cardiac arrhythmias, elucidating symptoms of cardiac disease, assessing risk of developing arrhythmias, and designing treatment for cardiac disease, is aided by study of the electrical activities of the heart. While various tools are available to medical personnel such as clinicians, physicians, heart function specialist, and caregivers for monitoring or studying the electrical activities of the heart, two common tools are the surface electrocardiogram ("ECG" or "EKG") and the intracardiac electrogram ("IEGM").

The electrocardiogram is a graphical recording as a function of time of the electrical voltage in the heart, produced noninvasively by the use of an electrocardiograph that measures electrical potential between various surface points of the body using a galvanometer. While various types of ECGs are known, one common type is the twelve lead ECG, which uses twelve leads placed on the limbs and chest to record information from particular parts of the heart. A group of leads known as the inferior leads measure electrical activity at the inferior region of the heart, essentially at the apex of the left ventricle. A group of leads know as the lateral leads measure electrical activity at the lateral wall of the heart, essentially the lateral wall of the left ventricle. A group of leads know as the anterior leads measure electrical activity at the anterior wall of the heart, essentially the frontal wall of the left ventricle. The ECG has a variety of uses, including as an indicator of whether the heart is performing normally or abnormally, or whether the heart muscle has acute or previous damage or is ischemic; for detecting potassium, calcium, magnesium and other electrolyte disturbances; for detecting conduction abnormalities such as heart blocks and in bundle branch blocks; as a screening tool for ischemic heart disease during an exercise tolerance test; as supplementing information on the physical condition of the heart such as left ventricular hypertrophy and mitral stenosis; and as an indicator of non-cardiac disease such as pulmonary embolism and hypothermia.

Electrocardiographs have some limited capability for audio communication, commonly offering tones for pulse (R-Wave). Pulse tones provide the clinician with a rough indication of normalcy. Although helpful, pulse tones are only of limited usefulness to medical personnel.

The intracardiac electrocardiogram is an invasive tool for the study of spontaneous cardiac activity and of cardiac responses to programmed electrical stimulation. Typically acquired by implantable cardiac devices such as pacemakers, implantable cardioverter defibrillators, and other types of implantable cardiac stimulation devices, the IEGM typically is obtained using leads placed in the left and right ventricles and the left and right atria. Implantable cardiac devices are usually configured to be used in conjunction with an external programmer that enables a physician to acquire data from and to control the operation of the implanted cardiac device. The external programmer may be configured to receive and display a wide variety of diagnostic information detected by the implantable device, such as, for example, IEGM signals sensed by the device. In addition, the external programmer may be configured to receive and display diagnostic data from other sources, such as from surface ECG devices. The external programmer also typically enables the physician to control the specific parameters by which the pacemaker detects arrhythmia conditions and responds thereto. For instance, the physician may specify the sensitivity with which the pacemaker or ICD senses electrical signals within the heart and also specify the amount of electrical energy to be employed in pacing pulses or defibrillation shocks. Another common control parameter is the A-VP delay, which for dual chamber devices specifies the time delay between a paced or sensed (i.e. native) atrial event and a paced ventricular event.

Implantable devices have also been provided with some limited capability for audio communication. Interrogation of an implantable medical device using audible sound communication is disclosed in U.S. Pat. No. 5,891,180, issued Apr. 6, 1999 to Greeninger et al. An implantable medical device includes an audio transducer that emits audible sounds including voiced statements or musical tones correlated to a device operating mode, state, operation, parameter value, programming or interrogation operating algorithm, or to a warning trigger event. However, even these sounds are of limited usefulness to medical personnel.

BRIEF SUMMARY

Advantageously, the present invention in at least some embodiments enables medical personnel to listen to musical notations that are linked to markers in a waveform of cardiac electrical activity, thereby increasing the level of care and safety of the patient. Advantageously, an application may use just one type of musical notation, or a number of different types of musical notations. Suitable types of musical notations includes tones of varying pitch, quality, duration, or combination thereof; series of tones; and tones and series of tones with different styles such as staccato, crescendo, and slur.

Advantageously, the present invention in at least some embodiments uses musically-represented cardiac markers to allow medical personnel to monitor the patient's cardiac electrical activity even when engaged in other work that prevents viewing of waveform data, and also to provide supplemental or confirmatory information to medical personnel when studying waveform data for diagnostic or other purposes.

Advantageously, the present invention in at least some embodiments provides musically-represented markers for signals from leads implanted into the heart. Advantageously, the present invention in at least some embodiments provides musically-represented markers for signals from different chambers of the heart.

Advantageously, the present invention in at least some embodiments links audio alerts as well as musical notations to cardiac markers. Advantageously, the present invention in at least some embodiments augments musically-represented markers with other audio information such as whether the patient is intrinsic or being paced, refractories, or other pacing and defibrillation information.

Advantageously, the present invention in at least some embodiments includes a programmer with or without a display or a remote unit with or without a display for medical personnel to listen to the rhythm of the musically-represented cardiac markers, to generate a report presenting the rhythm of the cardiac markers in visual form, or to do both.

One embodiment of the present invention is a method of monitoring electrical activity of the heart, which comprises acquiring time-based data relating to electrical activity of the heart; identifying characteristics of the data indicative of cardiac events, the cardiac events being of different types; and associating a musical notation with each of the identified characteristics in accordance with the type of cardiac event represented by each of the identified characteristics.

Another embodiment of the present invention is a method of monitoring electrical activity of the heart, which comprises acquiring a waveform of electrical activity of the heart; generating cardiac markers for characteristics of the waveform indicative of cardiac events, the cardiac events being of different types; linking a musical notation to each of the cardiac markers in accordance with the type of cardiac event represented by each of the cardiac markers; and reproducing the musical notations as sound effectively in synchronism with the waveform.

Another embodiment of the present invention is a method of monitoring electrical activity of the heart of a patient with a system having a sensing subsystem, an analysis subsystem, and an audio subsystem. The method comprises acquiring a cardiac waveform with the sensing subsystem; applying detection criteria to the cardiac waveform in the analysis subsystem to identify characteristics in the cardiac waveform indicative of cardiac events; generating cardiac markers in the analysis subsystem corresponding to the identified characteristics, the cardiac markers having time relationships effectively proportional to time relationships of the identified characteristics in the cardiac waveform; and reproducing the cardiac markers in accordance with the time relationships thereof as sound with the audio subsystem.

Another embodiment of the present invention is a system for monitoring electrical activity of the heart. The system comprises means for acquiring time-based data relating to electrical activity of the heart; means for identifying characteristics of the data indicative of cardiac events, the cardiac events being of different types; and means for associating a musical notation with each of the identified characteristics in accordance with the type of cardiac event represented by each of the identified characteristics.

Another embodiment of the present invention is an electrocardiograph system for monitoring electrical activity of the heart. The system comprises a sensing subsystem, an analysis subsystem, and an audio subsystem. The sensing subsystem comprises a plurality of surface electrodes for acquiring a surface ECG waveform. The analysis subsystem is coupled to the sensing subsystem for applying detection criteria to the ECG waveform to identify characteristics in the ECG waveform indicative of cardiac events, and for generating cardiac markers corresponding to the identified characteristics, the cardiac markers having time relationships effectively proportional to time relationships of the identified characteristics in the ECG waveform. The audio subsystem is coupled to the analysis subsystem for reproducing the cardiac markers in accordance with the time relationships thereof as sound.

Another embodiment of the present invention is an apparatus for monitoring electrical activity of the heart, comprising a communications subsystem, an analysis subsystem, and an audio subsystem. The communications subsystem is for receiving a cardiac waveform. The analysis subsystem is coupled to the sensing subsystem for applying detection criteria to the cardiac waveform to identify characteristics in the cardiac waveform indicative of cardiac events, and for generating cardiac markers corresponding to the identified characteristics, the cardiac markers having time relationships effectively proportional to time relationships of the identified characteristics in the cardiac waveform. The audio subsystem is for reproducing the cardiac markers in accordance with the time relationships thereof as sound.

Another embodiment of the present invention is an apparatus for monitoring electrical activity of the heart, comprising a communications subsystem and an audio subsystem. The communications subsystem is for receiving cardiac markers corresponding to identified characteristics in a cardiac waveform indicative of cardiac events, the cardiac markers having time relationships effectively proportional to time relationships of the identified characteristics in the cardiac waveform. The audio subsystem is coupled to the communications subsystem for reproducing the cardiac markers in accordance with the time relationships thereof as sound.

DETAILED DESCRIPTION

Cardiac electrical activity includes intrinsic signals as well as paced or stimulated signals. Waveforms of cardiac electrical activity may be detected by a variety of systems, including surface ECG systems and various implantable cardiac devices including implantable cardiac stimulation devices. Intrinsic cardiac signals and various cardiac conditions influence these waveforms in ways that can be identified using various detection criteria, and from which cardiac markers may be generated. Cardiac markers may be generated for pacing and stimulation signals, as well as for the occurrence of certain conditions and functionality, and the absence of certain conditions and functionality. Musical notations are linked to these cardiac markers as appropriate and are sounded as a function of time, thereby generating musical sound which is indicative of the patient's cardiac function. Just one type of musical notation such as tone, for example, may be used exclusively throughout a session, or different types of musical notations may be use in the session. Suitable types of musical notations include tones of varying pitch, quality, duration, or combination thereof; series of tones; and tones and series of tones with different styles such as staccato, crescendo, and slur. Musical notation in the form of intrusive auditory alerts, for example, may be used for the occurrence of specific conditions as well as for the absence of specific conditions or functionality. Other audio information may be provided, such as whether the patient is intrinsic or being paced, refractories, or other pacing and defibrillation information. Medical personnel may listen to this audible information to monitor cardiac electrical activity when the medical personnel is unable to look at a visually displayed waveform, and may even listen to this audible information to supplement their review and analysis of visually displayed waveforms and cardiac markers while perform diagnosis, research, or other medical tasks.

Figure 1:
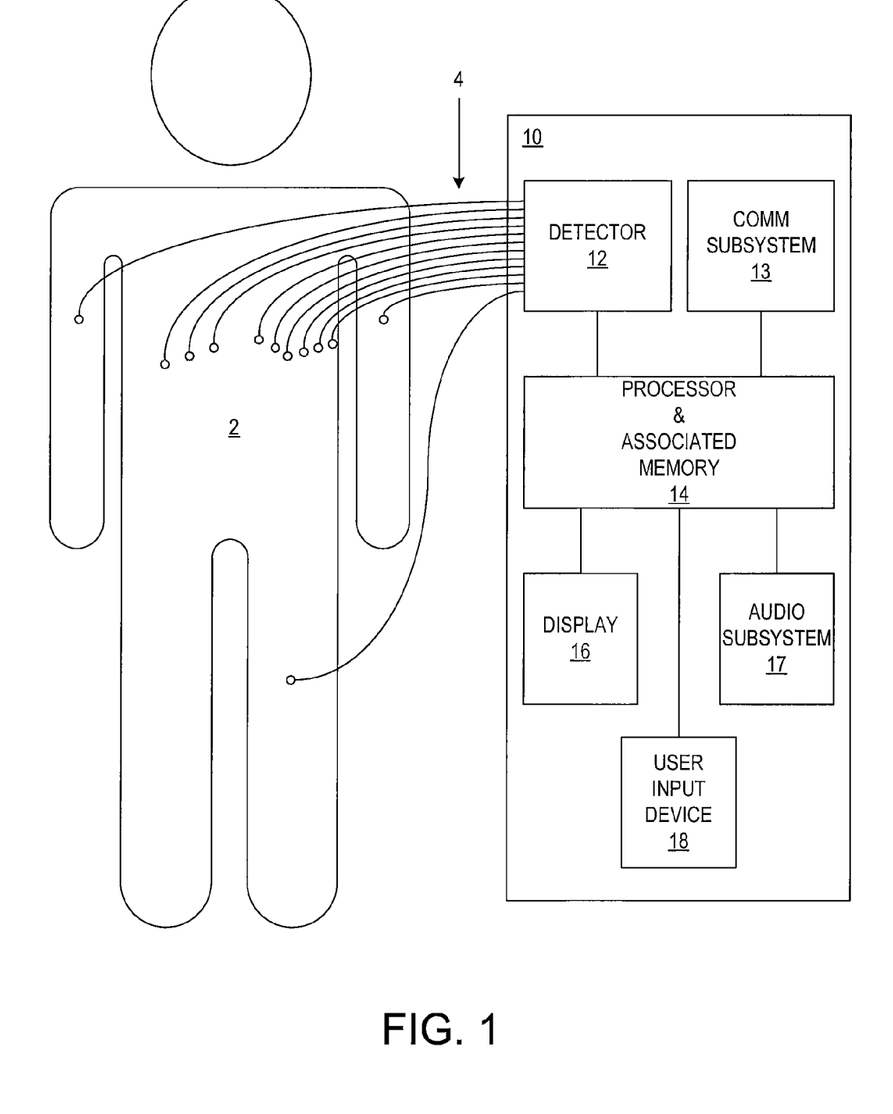
FIG. 1 is a schematic diagram of a twelve lead ECG system.
Figure 2:
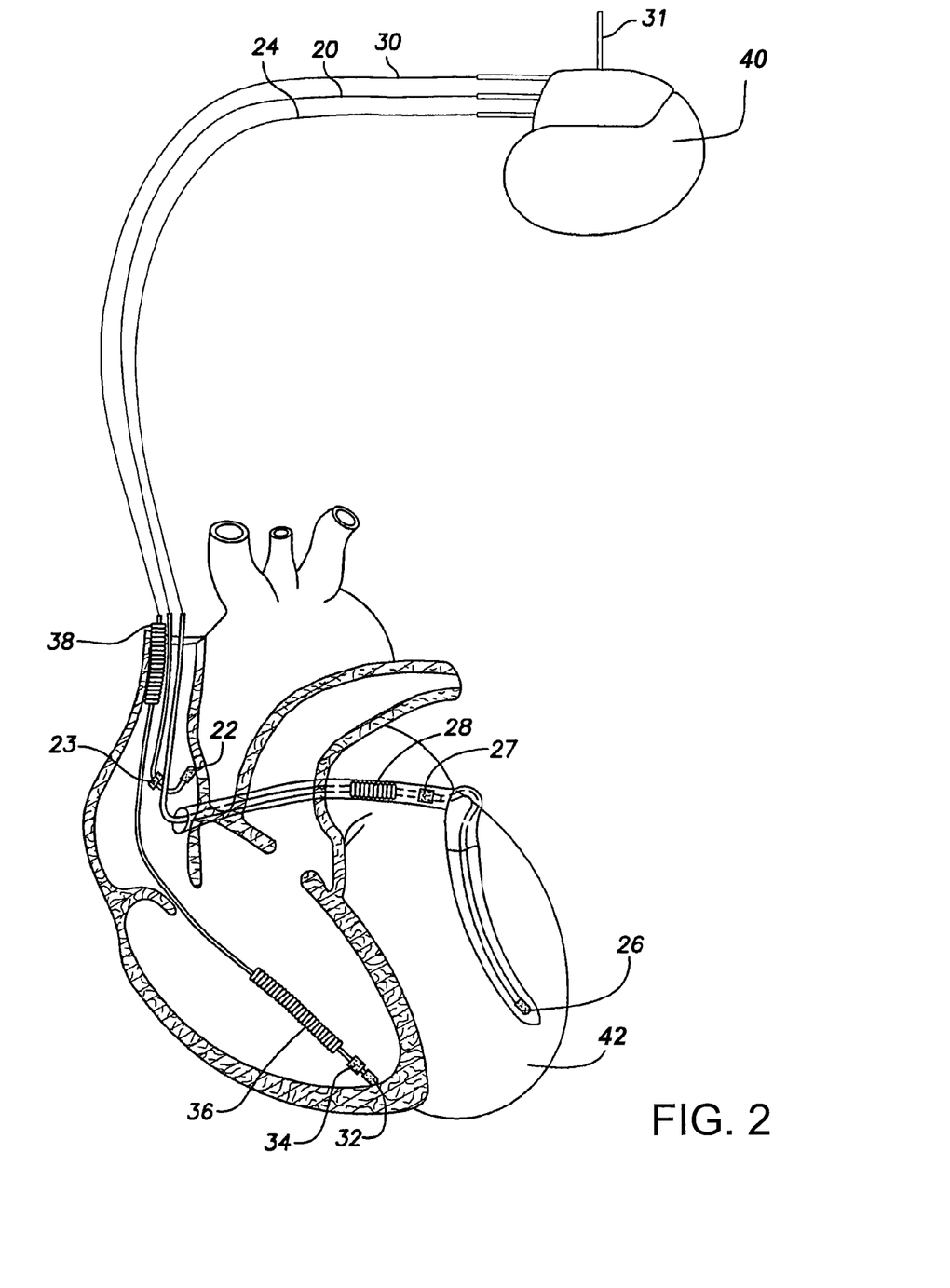
FIG. 2 is a simplified cross-sectional diagram of a heart having implanted leads for monitoring cardiac electrical signals and for delivering multi-chamber stimulation and shock therapy.
Figure 3:
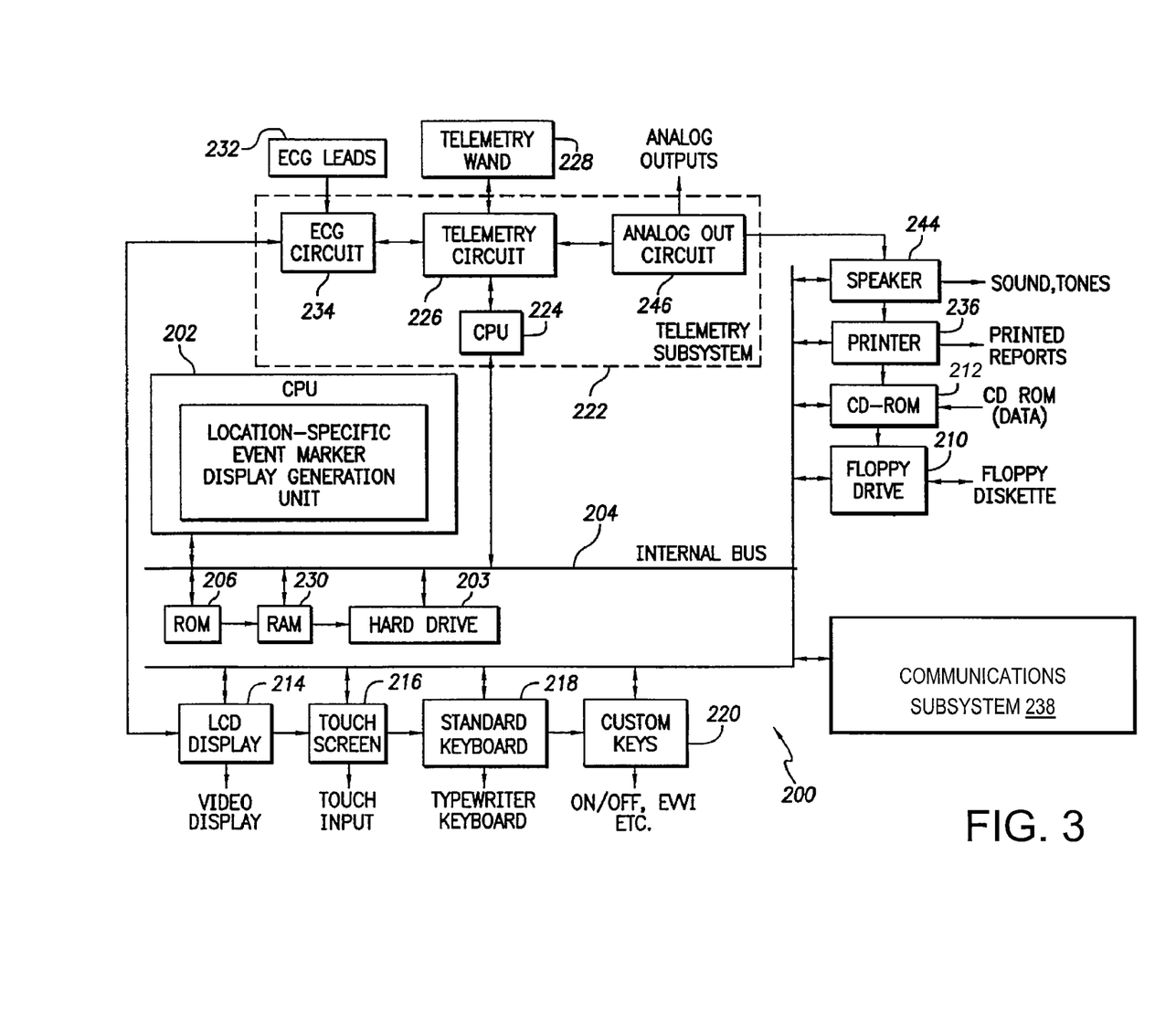
FIG. 3 is a schematic block diagram of a programmer suitable for communicating with an implantable cardiac device.
Figure 4:
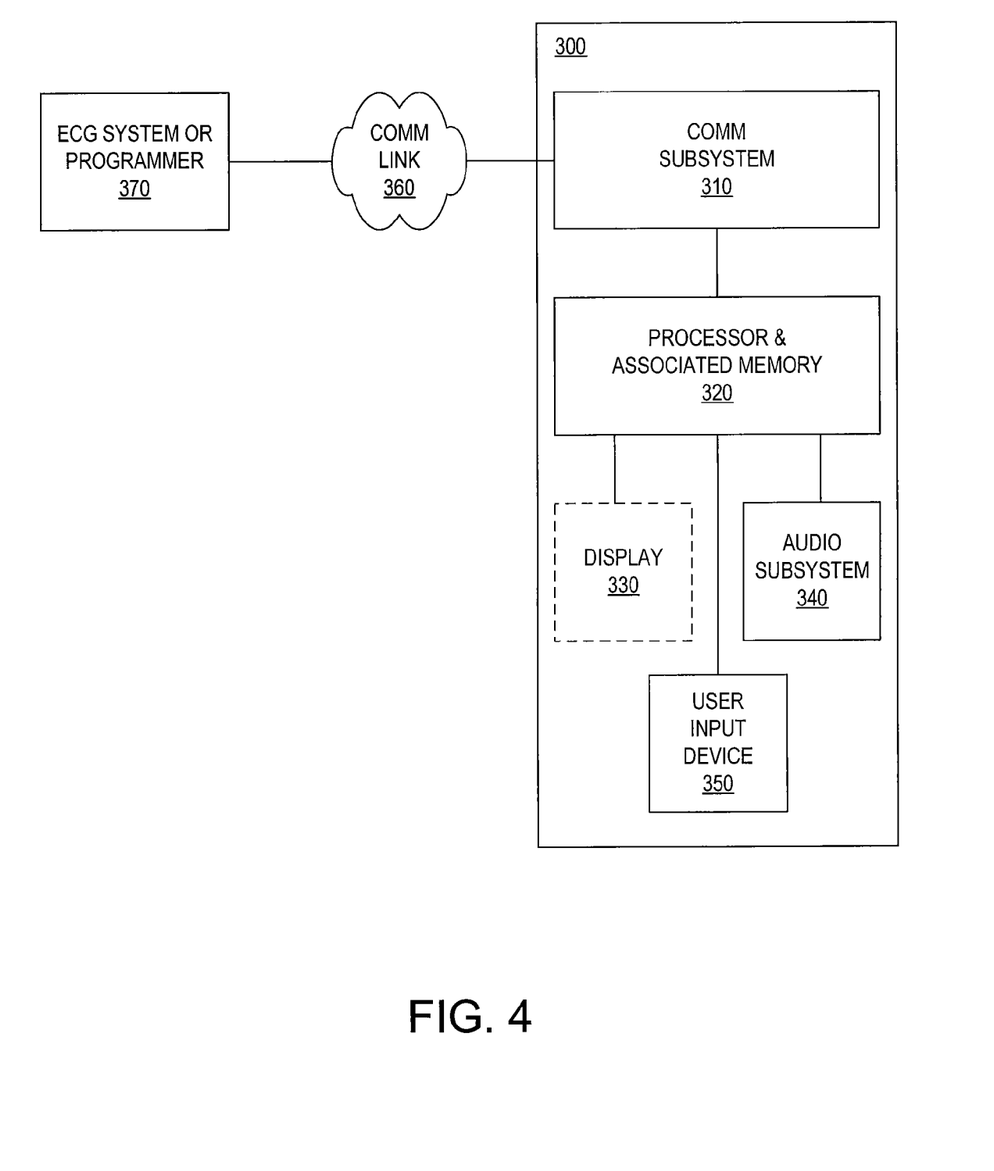
FIG. 4 is a schematic block diagram of a remote care unit.

The use of musically-represented cardiac markers to provide auditory information to medical personnel is useful in a wide variety of different patient care and diagnostic systems, including ECG systems such as ECG system 10 shown in FIG. 1, systems of implantable cardiac stimulation devices and programmers such as implantable cardiac stimulation device 40 shown in FIG. 2 and programmer 200 shown in FIG. 3, and remote care units such as remote care unit 300 shown in FIG. 4. Musically-represented cardiac markers also have may other uses, including in remote monitoring devices, real time telemetry receivers, bedside monitors, vital signs monitors, diagnostic equipment such as treadmills and bicycles, automated external defibrillators, monitor defibrillators, and combination systems. The cardiac markers themselves may be generated within one or several subsystems of a system. In the case of a surface ECG system, for example, the cardiac markers may be generated in the ECG system. In the case of a system that includes an implantable cardiac stimulation device and a programmer, cardiac markers may be generated in the implantable cardiac stimulation device and transmitted to the programmer, or the implantable cardiac stimulation device may transmit digitized waveforms or digitized waveform segments to the programmer which then processes the waveform data to obtain cardiac markers, or some cardiac markers may be generated in the implantable cardiac stimulation device and others generated in the programmer. In the case of a remote care unit, cardiac markers may be sent to the remote care unit or digitized waveforms or digitized waveform segments may be sent to the remote care unit wherein they are processed to obtain cardiac markers. A remote care unit may also be used as a replay unit to process a signal received from a remote server, personal computer, or programmer. Musically-represented cardiac markers may also be used in non-real time applications, such as when medical personnel study a recording of a patient's ECG or IEGM on a personal computer, personal data assistant, computer workstation, or a medical terminal. The musically-represented cardiac markers may be linked by time scale with a visual representation of the patient's cardiac-related waveform data, and either played so that the medical personnel may follow visually, or played for particular waveform segments as selected by the medical personnel. The speed at which the musically-related cardiac markers may be played may be the actual speed, or the speed may be reduced or increased as desired. Preferably, musical notations are linked to the cardiac markers in the device having the user interface, illustratively a surface ECG system, a programmer, or a remote care unit, although if desired musical notations may be linked to the cardiac markers ahead of the user's device, with the musical notations and tempo information being transmitted to the user's device without the cardiac markers.

FIG. 1 shows an illustrative surface ECG system 10 that includes musically-represented cardiac markers. While the surface ECG system 10 is based on a twelve lead system having a bundle of leads 4, many other types of surface ECG systems are well known or are commercially available, and may be modified in accordance with the teachings and suggestions described herein. The leads 4 terminate in electrode sensors that are placed on the chest and limbs of a patient 2 to sense electric signals. Electrical signals sensed by the leads 4 are detected by a signal detector 12, where various actions such as signal amplification and digital-to-analogue conversion may occur. The digitized signals are furnished to a processor and associated memory 14 for processing into an ECG waveform and for analysis and cardiac marker generation. The resulting ECG waveform is displayed by a display device 16 (which may be a monitor or a printer, for example), and a musical representation of the cardiac markers is sounded by an audio subsystem 17 (which may include a speaker or headphones and a suitable amplifier, for example). User interaction is enabled by a user input device 18, which may be a keyboard, touch screen, mouse, voice recognition, or another type of device for interacting with a user. The surface ECG system 10 may be implemented in digital, analogue, or a combination thereof, and in hardware, software, or a combination thereof.

FIG. 2 shows an illustrative implantable cardiac stimulation device 40 with implanted leads for monitoring cardiac electrical signals and for delivering multi-chamber stimulation and shock therapy. While the implantable stimulation device 40 is based on a three lead system having leads 20, 24 and 30 and produces a four-chamber IEGM, many other types of implantable devices and lead systems are well known or are commercially available, including monitoring devices with and without stimulation capability, and may be modified in accordance with the teachings and suggestions described herein.

Stimulation device 40 is in electrical communication with the heart 42 of a patient through three leads 20, 24 and 30, which are suitable for sensing electrical activity of the heart and for delivering multi-chamber stimulation and shock therapy. Lead 20 is an implantable right atrial lead that is used to sense atrial cardiac signals and to provide right atrial chamber stimulation therapy. The lead 20 has an atrial tip electrode 22, which typically is implanted in the right atrial appendage, and an atrial ring electrode 23. The lead 24 is a coronary sinus lead that is used to sense left atrial and ventricular cardiac signals and to deliver left ventricular chamber pacing therapy. The lead 24 has a left ventricular tip electrode 26, a left atrial ring electrode 27, and a left atrial coil electrode 28. The lead 24 is placed in the coronary sinus region via the coronary sinus. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. The lead 30 is an implantable right ventricular lead that is used to receive cardiac signals and deliver stimulation in the form of pacing and shock therapy to the right ventricle. The lead 30 has a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. An additional electrode 31 is provided in proximity to the device can to provide a "tickle warning" signal.

One suitable implantable cardiac stimulation device is described in detail in U.S. Pat. No. 6,748,274 issued Jun. 8, 2004 to Levine et al., which hereby is incorporated herein in its entirety by reference thereto.

An external programmer may be used for programming an implantable cardiac stimulation device such as the implantable cardiac stimulation device 40 shown in FIG. 2. A programmer permits a physician or other user to program the operation of the implanted device and to retrieve and display information received from the implanted device such as IEGM data and device diagnostic data. In particular, the programmer is provided with internal components capable of separately receiving, storing and processing cardiac markers representative of events paced or sensed in any of the four chambers of the heart. Additionally, the external programmer may receive and display surface ECG data from ECG leads attached to the patient. Depending upon the specific programming of the external programmer, the programmer may also be capable of processing and analyzing data received from the implanted device and from the ECG leads to, for example, render preliminary diagnosis as to medical conditions of the patient or to the operations of the implanted device.

FIG. 3 shows an example of a suitable programmer 200. Operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 203, floppy drive 210, and CD ROM drive 212, or other suitable permanent mass storage device.

In operation, the programmer 200 displays a menu of programming options to the user on an LCD display 214 or other suitable computer display device. The menu may, for example, be a list of specific programming parameters of the implanted device to be programmed or may display a menu of types of diagnostic data to be retrieved and displayed. In response thereto, the user, typically a physician, enters various commands via either a touch screen 216 overlaid on the LCD display or through a standard keyboard 218 supplemented by additional custom keys 220, such as an EVVI key.

The physician initially controls the programmer 200 to retrieve IEGM and other data stored within the implanted cardiac stimulation device. To this end, CPU 202 transmits appropriate signals to a telemetry subsystem 222, which provides components for directly interfacing with the implanted device. Telemetry subsystem 222 may include its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. Note that the telemetry wand 228 may be wireless or hardwired. Typically, at the beginning of the programming session, the external programming device commands the implanted device to output all previously recorded patient and device diagnostic information. The data provided by the stimulation device and the cardiac markers displayed by the external programmer distinguish among a greater number of sensing locations, such as between the left and right chambers of the heart or among multiple locations within a single chamber of the heart. In the primary example described herein, the memory of the external programmer stores the location-specific event records, counter data and IEGM data for each of the four chambers of the heart received from the stimulation device. Data retrieved from the implanted device is stored by external programmer 200 either within a random access memory (RAM) 230, hard drive 208 or within removable media such as a floppy diskette placed within a removable media drive, illustratively floppy drive 210.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 may receive ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time. Thus the programmer may receive data both from the implanted device and from the external ECG leads.

A speaker 244, which may be piezoelectric or any other suitable type, is included for providing audible tones to the user, including conventional tones such as a warning beep in the event the physician provides improper input, as well as novel tones as described below. Telemetry subsystem 222 additionally includes an analog out circuit 246 for controlling the transmission of analog output signals.

Many of these aspects of the programmer 200 are described in further detail, along with reprogramming techniques, in U.S. Pat. No. 6,748,274 issued Jun. 8, 2004 to Levine et al., which hereby is incorporated herein in its entirety by reference thereto. Illustrative techniques for programming an implanted cardiac stimulation device may also be found in U.S. Pat. No. 5,716,382 issued Feb. 10, 1998 to Snell, which hereby is incorporated herein in its entirety by reference thereto. Further disclosure pertaining to illustrative information that may be displayed using the programmer may be found in U.S. Pat. No. 5,974,341 issued Oct. 26, 1999 to Er et al., which hereby is incorporated herein in its entirety by reference thereto.

While a speaker may be integrated with the programmer 200, the speaker or headphones may be provided externally if desired. The audio port may be analogue or digital, such as a USB port, and may also be wireless, such as MICS or Bluetooth.

Where the programmer 200 is capable of providing musically-represented cardiac markers for the three channels of an IEGM as well as a fourth channel for the surface ECG, the user may be provided with the capability of selecting any one or any combination of the channels. Suitable techniques for turning the channels on or off include the use of a fly out menu tab, and a button on the speaker, headphone, or programmer.

As shown in FIG. 4, routine and emergency medical services may be provided to a patient over a communications link 360 using a remote care unit 300. A system 370 located with the patient may be an ECG system, a programmer for an implantable cardiac device implanted in the patient, or other system or device capable of acquiring cardiac waveform data such as ECG and IEGM waveform data and identifying cardiac markers therein. The system 370 is capable of communicating cardiac markers to the remote care unit. While the system 370 and the remote care unit 300 may optionally be provided with the capability of communicating ECG and IEGM waveform data, the bandwidth requirements are considerable. However, cardiac markers do not necessarily have high bandwidth requirements, and may be used where sufficient bandwidth is not available, or as an audible supplement to a remote evaluation of the patient using waveform images.

The remote care unit 300 illustratively includes a processor and associated memory 320, a communications subsystem 310 for receiving cardiac marker data, or optionally waveform data from which cardiac markers may be derived, and an audio subsystem 340 for making audible the cardiac markers. A user input device 350 is included to facilitate user control of the remote care unit 300, while an optional display 330 may or may not be included depending on whether waveform data is to be displayed.

The communications link 360 may be any type of remote communications link, including low bandwidth dial-up over the public switched telephone network, moderate bandwidth over wireless communications such as WiFi, cable and ISDN, and high bandwidth over high speed cable, ISDN and T1 lines. Communications may also be over local area networks, including wired networks such as Ethernet and wireless networks such as WiFi, over wired direct connections such as serial, parallel and USB, and over short range wireless connections such as Bluetooth.

Other techniques may be used for communicating cardiac markers. Illustratively, cardiac markers may be sent as telemetry from an implanted cardiac device to a remote receiver in real time or near real time using radio frequency signals, acoustical signals, ultrasonic signals, magnetic signals, or any other type of signal transmission. Illustratively, the signals are encoded in digital or analogue form with the cardiac markers, and are interpreted and processed at the remote receiver. Illustrative techniques for remotely communicating cardiac markers are described in, for example, U.S. Pat. No. 4,791, 936 issued Dec. 20, 1988 to Snell et al., which hereby is incorporated herein in its entirety by reference thereto.

Many different types of cardiac markers are known, and others may be envisioned by medical personnel. Generally speaking, waveforms of cardiac electrical activity may be processed to identify a variety of cardiac markers for specific waveform characteristics indicative of intrinsic cardiac electrical activity, such as those indicative of the R-wave, P-wave, and QRS complex, or the absence of such waves or other functionality as may occur from, for example, a skipped beat. Tones may be linked to these types of cardiac markers. Another type of cardiac marker is indicative of pacing and stimulation signals, such as an atrial pacing signal or a ventricular pacing signal. Tones may be linked to these types of cardiac markers. Another type of cardiac marker is indicative of segments such as the QT segment. Tones may be linked to these types of cardiac markers. Another type of cardiac marker is based on relationships between waveform characteristics of interest, or on relationships between the same waveform characteristic of interest as found in different cardiac cycles. Tones or alerts may be linked to these types of cardiac markers. Another type of cardiac marker is generated based on relationships between characteristics of interest in the patient's waveform data and the same characteristics in a reference database. Tones or alerts may be linked to these types of cardiac markers. Other types of cardiac markers may be generated for specific serious conditions as indicated by certain sequences in the waveform, such as atrial fibrillation ("AF"). Intrusive auditory alerts may be linked to these cardiac markers to indicate the problem.

Figure 5:
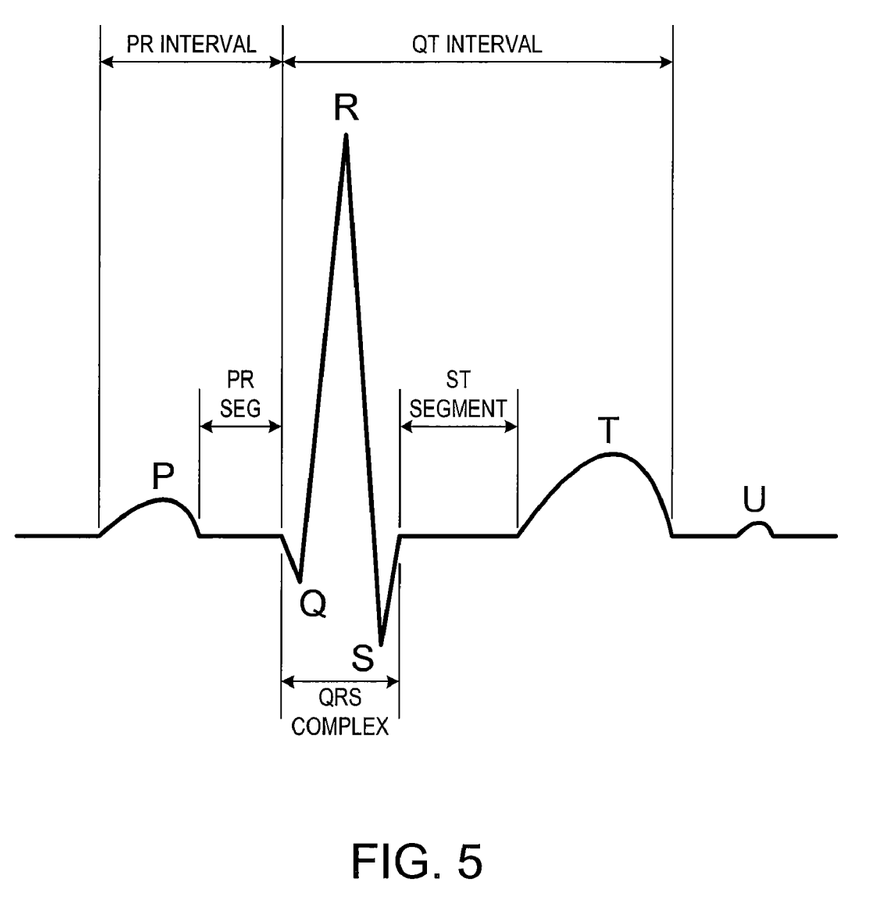
FIG. 5 is a graph showing an idealized normal electrocardiogram waveform for a complete cardiac cycle.

To better appreciate how musically-represented cardiac markers may be used in the ECG system 10 of FIG. 1, for example, consider the idealized normal electrocardiogram waveform for a complete cardiac cycle shown in FIG. 5. The normal ECG includes a P wave, a QRS complex and a T wave. A small U wave is not normally visible, although it is shown in FIG. 5 for completeness.

The P wave is the electrical signature of the current that causes atrial contraction. Its relationship to the QRS complex determines the presence of a heart block. Irregular or absent P waves may indicate arrhythmia. The shape of the P waves may indicate atrial problems.

The QRS complex corresponds to the current that causes contraction of the left and right ventricles. The Q wave, when present, represents the small horizontal (left to right) current as the action potential travels through the interventricular septum. Very wide and deep Q waves do not have a septal origin, but may indicate myocardial infarction that involves the full depth of the myocardium and has left a scar. The R and S waves indicate contraction of the myocardium itself. Abnormalities in the QRS complex may indicate bundle branch block, ventricular origin of tachycardia, ventricular hypertrophy or other ventricular abnormalities. The complexes are often small in pericarditis or pericardial effusion.

The T wave represents the repolarization of the ventricles. The QRS complex usually obscures the atrial repolarization wave so that it is not usually seen. Inverted T waves can be a sign of disease, although an inverted T wave is normal in some patients. Other T wave abnormalities may indicate electrolyte disturbance, such as hyperkalemia or hypokalemia.

The ST segment connects the QRS complex and the T wave and is usually level with the PR segment. Upward or downward displacement may indicate damage to the cardiac muscle or strain on the ventricles. It can be depressed in ischemia and elevated in myocardial infarction or Brugada syndrome, and upslopes in digoxin use.

The U wave is not always seen, as it is quite small. Prominent U waves are most often seen in hypokalemia, but may be present in hypercalcemia, thyrotoxicosis, or exposure to digitalis, epinephrine, and Class 1A and 3 antiarrhythmics, as well as in congenital long QT syndrome and in the setting of intracranial hemorrhage. An inverted U wave may represent myocardial ischemia or left ventricular volume overload.

The QT interval is measured from the beginning of the QRS complex to the end of the T wave. The QT interval as well as the corrected QT interval are important in the diagnosis of long QT syndrome and short QT syndrome. The QT interval varies based on the heart rate, and various correction factors have been developed to correct the QT interval for the heart rate.

The PR interval is measured from the beginning of the P wave to the beginning of the QRS complex. A prolonged PR indicates a first degree heart block, while a shorting may indicate an accessory bundle that depolarizes the ventricle early, such as seen in Wolff-Parkinson-White syndrome The ECG system 10 also is capable of measuring the propagation axis, which is the general direction of the electrical impulse through the heart. It is usually directed to the bottom left, and extreme deviation that is not attributable to tallness or obesity may indicate a bundle branch block, ventricular hypertrophy or pulmonary embolism.

The normal P-wave, R-wave, Q-wave, QRS complex, T-wave, ST segment, QT interval, PR interval, axis; deviations from normalcy in these waves, segments and intervals; the absence of certain of these waves, and the presence of a U-wave may be detected and used to generate appropriate cardiac markers. Techniques for identifying various waveform characteristics for specific portions of the cardiac waveform are well known, and include absolute and relative amplitude, slope, amplitude peak, maximum slew rate, power spectral density, elapsed time, integration, inversion, interval as a function of amplitude level, histograms, and so forth. Once cardiac markers are generated, different musical notations may be linked to the cardiac markers. A QT segment, for example, may be represented by a long low note, while the Q wave and the T wave may be represented by respective short tones of different pitch and/or quality superimposed on the long low tone.

Cardiac markers may also be generated from an IEGM, either alone or along with a surface ECG. An illustrative apparatus for generating and displaying cardiac markers adjacent to IEGM and surface ECG signal is described in U.S. Pat. No. 4,791,936 issued Dec. 20, 1988 to Snell et al., which hereby is incorporated herein in its entirety by reference thereto. Additional techniques are described in U.S. Pat. No. 5,954,666 issued Sep. 21, 1999 to Snell, which hereby is incorporated herein in its entirety by reference thereto.

Figure 6:
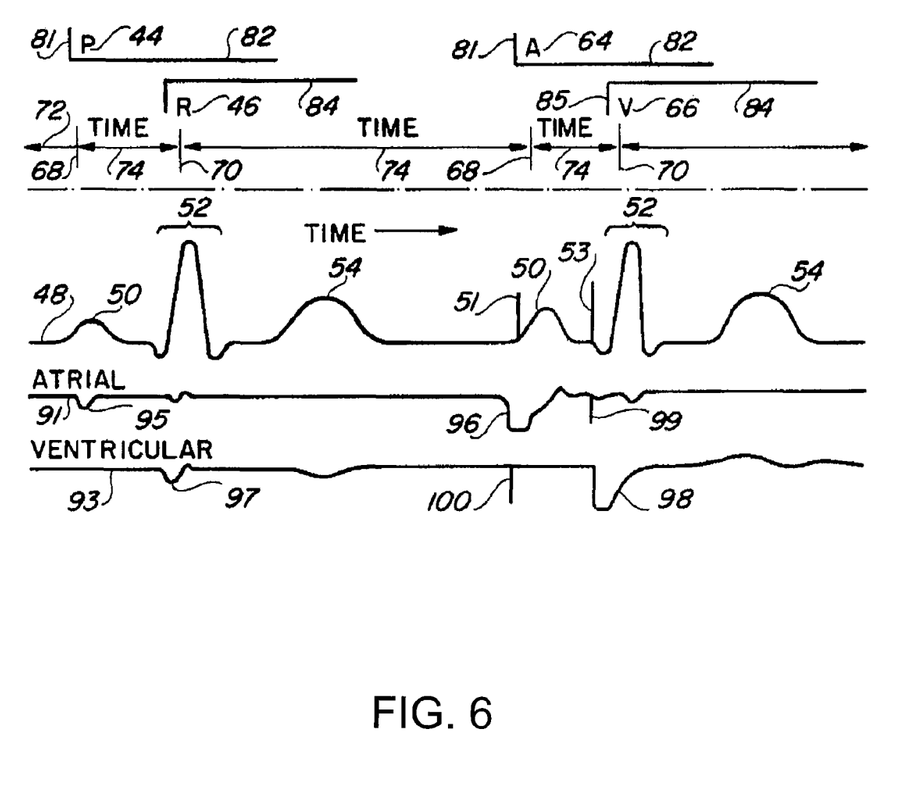
FIG. 6 is a set of graphs showing ECG and IEGM waveforms and corresponding markers for two cardiac cycles.

Illustrative IEGM and surface ECG waveforms and stimulation/pacing signals along with an illustrative set of cardiac markers obtained from them is shown in FIG. 6, which is taken from the aforementioned '936 Snell et al. patent. Surface ECG 48 contains two complete cardiac cycles, each of which includes a P-wave 50, QRS complex 52, and T-wave 54. The second cycle also includes spikes 51 and 53, which are indicative of pacing pulses. The IEGM includes an atrial intracardiac waveform 91 and a ventricular intracardiac waveform 93. The atrial intracardiac waveform 91 includes sinus P-wave 95, which indicates natural atrial depolarization, and a paced or stimulated atrial depolarization P-wave 96. The pulse 99 is a far-field ventricular pulse or V-pulse, which arises from stimulation of the ventricle and is termed "far-field" because it occurs in a different chamber of the heart from the one being sensed. The ventricular intracardiac waveform 93 includes an indication 97 of natural ventricular depolarization (QRS complex), far-field atrial pulse or A-pulse 100, and paced ventricular depolarization R-wave 98.

Various information including cardiac markers may be determined from the waveforms 48, 91 and 93. The information may if desired be displayed along with the waveforms 48, 91 and 93, and various tones and alerts may be linked to the cardiac markers for audio reproduction. Cardiac events such as the intrinsic P-wave and R-wave in the first cardiac cycle are identified and represented by the P and R symbols 44 and 46. Although the T-wave is identifiable, it is not used to generate a cardiac marker in this example, although it may be so used if desired. Two more cardiac events occur In the second cardiac cycle, namely an atrial pulse 96 output by an implantable cardiac stimulation device to depolarize the atrium, which is represented by the symbol "A," and a ventricular pulse 98 output by an implantable cardiac stimulation device to depolarize the ventricle, which is represented by the symbol V. The pulses 96 and 98 also are detected by the IEGM electrodes, and appear as the spikes 51 and 53 in the surface ECG.

Responsive to the detection of the P-wave, R-wave, atrial pulse A, and ventricular pulse V, cardiac markers 68 and 70 for each of the cardiac cycles are generated. The cardiac markers 68 and 70 indicate the specific point of depolarization of the atrium and ventricle as indicated in the first cardiac cycle by an intrinsic P-wave and an intrinsic R-wave, and as caused in the second cycle by an atrial pulse an a ventricular pulse from an implantable cardiac stimulation device.

The elapsed time between any two cardiac events may also be determined, as indicated by intervals 74. Although the time periods 74 are for time between consecutive events, time periods may be determined between any two events whether consecutive or not.

The programmed and/or actual refractory periods of the atrium and ventricle as set or measured by the implantable cardiac stimulation device may be determined, and is represented in FIG. 6 by horizontal indicators 82 and 84. The horizontal indicator extends from the cardiac event to the end of the respective refractory period. The atrial refractory period has vertical section 81 which extends upward from horizontal line 82. The ventricular refractory period has vertical section 85 which extends down from horizontal line 84. This proves to be helpful information in determining whether the implantable cardiac stimulation device has been programmed with the proper refractory period. If the T-wave is not totally enclosed in the refractory period of the "P" or "A," it could cause another depolarization of the atrium. If the refractory period is too short for the characteristics of a particular heart, an alert cardiac marker may be generated.

The various ways in which medical information is conveyed to medical personnel may be made selectable. Medical personnel may select either musically-represented cardiac markers, visual cardiac markers, the surface ECG 48, the atrial intracardiac waveform 91, the ventricular intracardiac waveform 93, or various combinations thereof, depending on the interests of the medical personnel and the capabilities of the user's device.

Figure 7:
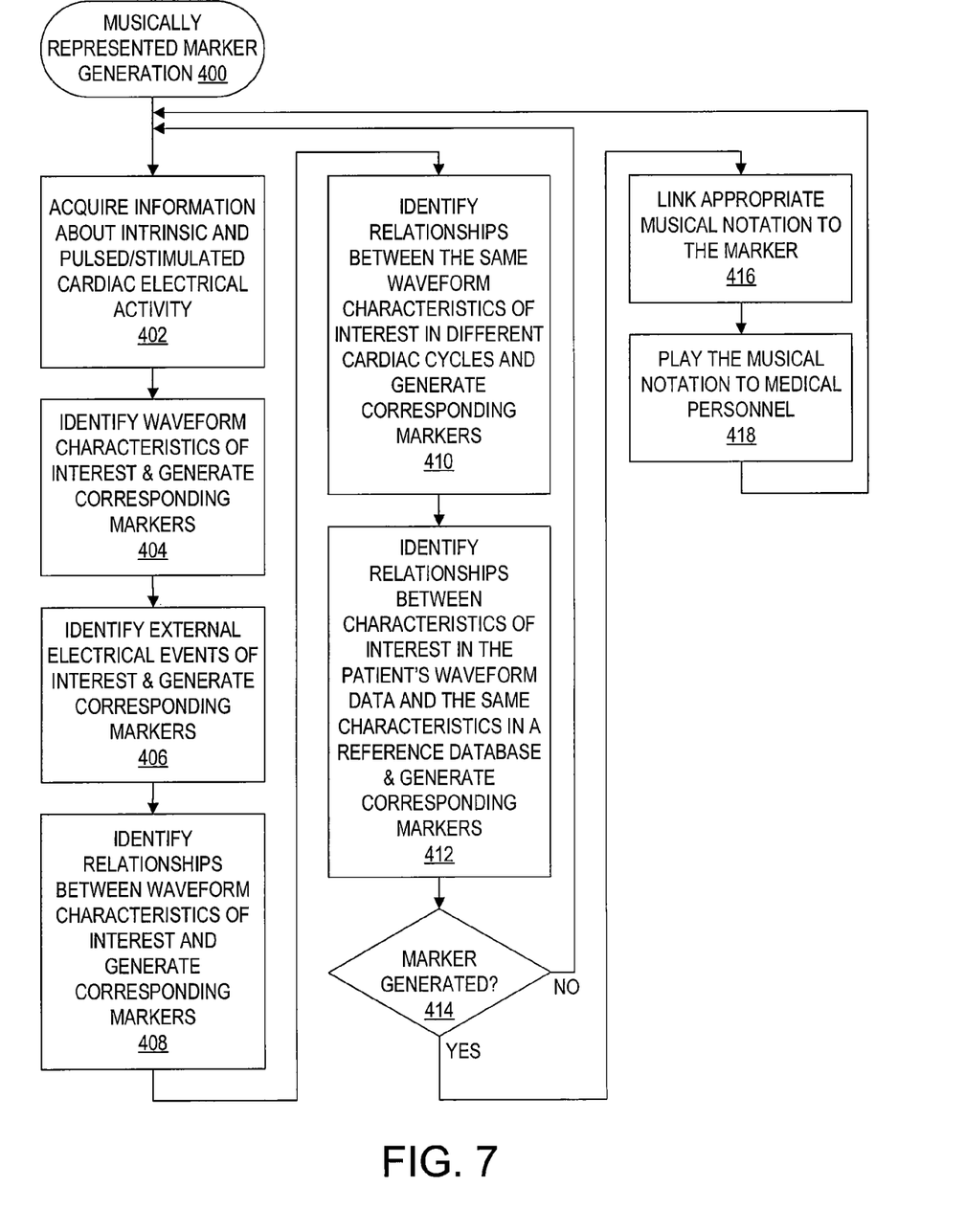
FIG. 7 is a flowchart showing a process for generating musically-represented cardiac markers.

FIG. 7 is a flowchart showing a general process 400 for generating cardiac markers and linking tones to cardiac markers. Information is acquired about intrinsic and pulsed or stimulated cardiac electrical activity (block 402). This information may be in the form of waveforms of electrical activity over time such as ECGs and IEGMs, but may also be information such as the time that a particular atrial or ventricular pacing signal is generated by an implantable cardiac stimulation device. In a real time or near real time system, the performance of subsequent operations in the process 400 preferably is multitasked with continued acquisition of information about intrinsic and pulsed or stimulated cardiac electrical activity. For non-real time applications, all of the cardiac electrical activity information may be acquired before the rest of the process 400 is performed.

The operations represented by blocks 404, 406, 408, 410 and 412 are representative of some of the types of cardiac markers that may be generated, and are not intended to limit the type of cardiac markers contemplated by the inventor. Moreover, the operations represented by blocks 404, 406, 408, 410 and 412 are optional, and any particular system may be designed to perform any one or any combination of the operations, or the particular system may provide the user with the capability of selecting the type of operations to be performed.

One type of cardiac marker is generated based on waveform characteristics of interest (block 404). This type of cardiac marker includes P-waves, R-waves, the QRS complex, T-waves, U-waves, relative amplitude of the ST segment, the duration of the QT interval, the duration of the PR interval, the direction of the propagation axis, atrial stimulating appearing in a surface ECG or ventricular intracardiac waveform, and ventricular stimulation appearing in a surface ECG or atrial intracardiac waveform. Waveform characteristics may include amplitude, shape, slope, interval, integration area, wave width, and so forth. The absence of a wave may also be considered to be a waveform characteristic of interest.

Another type of cardiac marker is generated based on external electrical events of interest (block 406). This type of cardiac marker includes timing information about atrial and ventricular pulses acquired directly from an implantable cardiac stimulation device.

Another type of cardiac marker is generated based on relationships between waveform characteristics of interest (block 408). The relationships may include abnormal relative amplitudes of various wave types.

Another type of cardiac marker is generated based on relationships between the same waveform characteristic of interest as found in different cardiac cycles (block 410). A change in the QRS complex is illustrative.

Another type of cardiac marker is generated based on relationships between characteristics of interest in the patient's waveform data and the same characteristics in a reference database (block 412). Comparative histograms are illustrative.

Another type of cardiac marker may be generated for specific conditions as indicated by certain sequences in the waveform, such as atrial fibrillation ("AF").

Another type of cardiac markers may be generated from triggers such as are disclosed in United States Patent Application Publication No. 2005/0010120 published in the name of Jung et al. on Jan. 13, 2005, which hereby is incorporated herein in its entirety by reference thereto. The ECG system of the Jung et al. patent publication includes a database that stores recognized ECG signal triggers and corresponding diagnosis. The triggers refer to conditions that indicate the likelihood of arrhythmia. For example, triggers can include sinus beats, premature sinus beats, beats following long sinus pauses, long-short beat sequences, R on T-wave beats, ectopic ventricular beats, premature ventricular beats, and so forth. Triggers may include threshold values that indicate arrhythmia, such as threshold values of ST elevations, heart rate, increase or decrease in heart rate, late-potentials, abnormal autonomic activity, and so forth. A left bundle-branch block diagnosis can be associated with triggers such as the absence of q wave in leads I and V6, a QRS duration of more than 120 msec, small notching of R wave, and so forth. Triggers may also be based on a patient's history; for example the percentage of abnormal beats detected during an observation period, the percentage of premature or ectopic beats detected during an observation period, heart rate variation during an observation period, and so forth. Triggers may also include, for example, the increase or decrease of ST elevation in beat rate, the increase in frequency of abnormal or premature beats, and so forth. Methods such as computer-implemented logic rules, classification trees, expert system rules, statistical or probability analysis, pattern recognition, database queries, artificial intelligence programs and others can be used to match the separated signals with stored triggers.

Cardiac markers may also be generated from various advanced IEGM processing techniques, including distinguishing between cardiac ischemia, hypoglycemia and hyperglycemia as described in United States Patent Application Publication No. 2006/0167519 published in the name of Gill et al. on Jul. 27, 2006, United States Patent Application Publication No. 2006/0167518 published in the name of Gill et al. on Jul. 27, 2006, and United States Patent Application Publication No. 2006/0167365 published in the name of Bharmi on Jul. 27, 2006; creating location-specific diagnostic information as described in U.S. Pat. No. 6,748,274 issued Jun. 8, 2004 to Levine et al.; and monitor progression of congestive heart failure as described in U.S. Pat. No. 6,512,953 issued Jan. 28, 2003 to Florio et al., all of which hereby are incorporated herein in their entirety by reference thereto.

When a cardiac marker is generated (block 414-yes) in a real time system, the appropriate musical notation is linked to the cardiac marker (block 416) and the musical notation is played to medical personnel (block 418). Illustrative rules for linking tones or alerts to cardiac markers are as follows. It will be appreciated that the specific rules described herein are only illustrative, and are not intended to limit the type of rules contemplated by the inventor. All rules may be applied or only selected rules may be applied, as desired. Moreover, rules may be varied as desired, and some tones and rules may be suitable for a hospital setting while others may be suitable for a home care setting.

(1) Tones and alerts are linked to cardiac markers and played as a function of time to provide optional continuous auditory feedback.

(2) When applied to an IEGM, different pitch of tones are used for each of the channel, namely the atrium, right ventricle, and left ventricle.

(3) When applied to an IEGM, all three channels may independently be turned on or off. When a surface ECG is also used, the surface ECG channel may independently be turned on or off.

(4) The amplitude of a signal is reflected by the volume of the tone.

(5) An optional tonal variation such as a sharp or flat is used to reflect non-intrinsic rhythms.

(6) Basic and advanced tones, corresponding to basic and advanced cardiac markers, are used.

(7) Basic and advanced tones may be turned on and off independent of cardiac markers.

(8) Alerts such as missing beats, mode switch, atrial fibrillation, and so forth are represented by a series of irritating tones that get the attention of the medical personnel.

(9) Different instruments or their equivalents may be used for increased effect. For example, a symbol crash can represent a shock delivered when playing back a stored EGM.

Figure 8A:
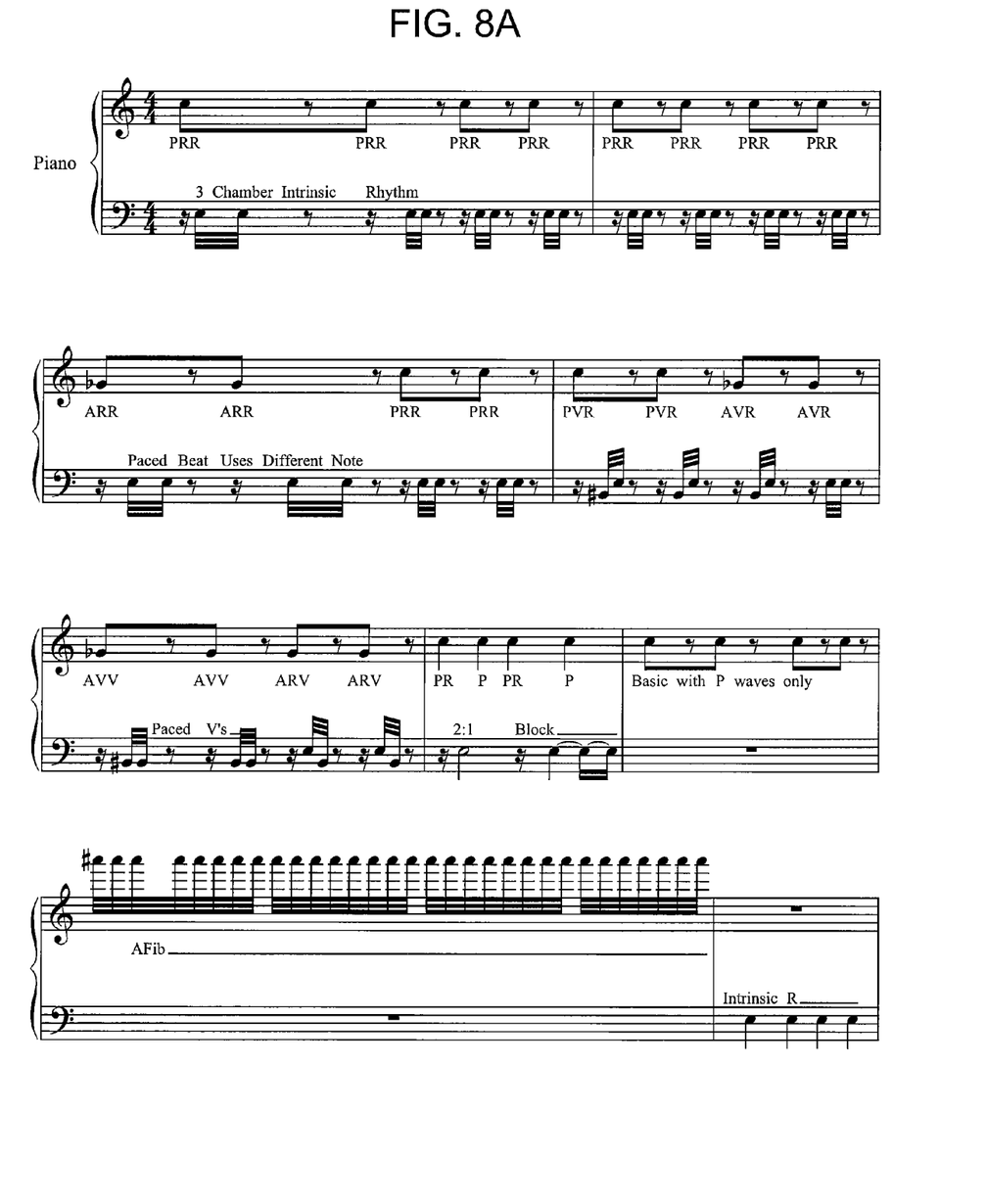
FIGS. 8A and 8B are a musical score showing illustrative linkage of musical notations to cardiac markers.
Figure 8B:
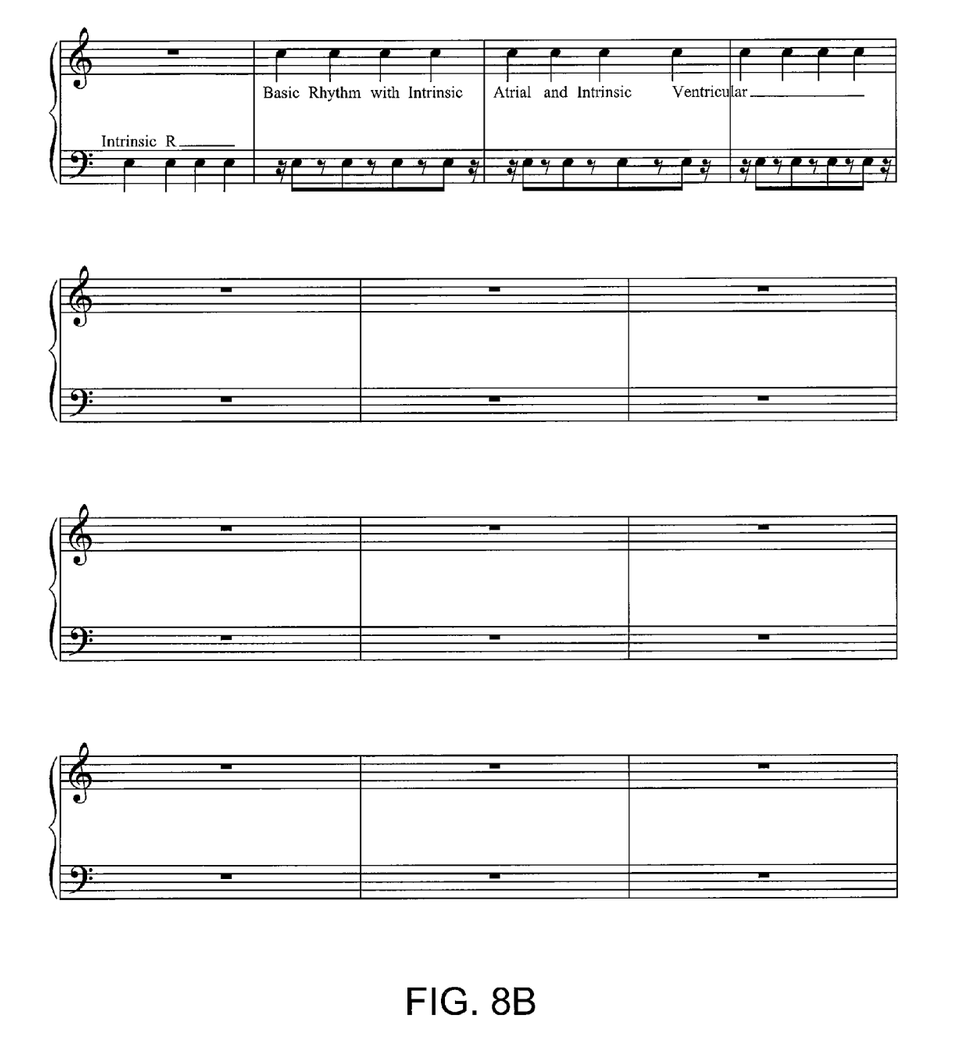

FIG. 8 is a musical score showing an illustrative application of some of the techniques described herein. Tones linked to the chamber intrinsic rhythm PRR are shown in the first two measures. Tones linked to a paced atrium ARR followed by intrinsic waves PRR are shown in the third measure. Various combinations of intrinsic and pacing signals PVR, AVR, AVV, and ARV are shown in the fourth and fifth measures. The sixth measure shows block, as indicated by PR followed by P only. Tones linked to a basic P-wave signal only are shown in the seventh measure. An atrial fibrillation alert is shown in the eighth measure. Tones linked to an intrinsic R wave signal only are shown in the ninth measure. Tones linked to a basic rhythm with intrinsic atrial and intrinsic ventricular signals are shown in the tenth, eleventh and twelfth measures.

While digital processing techniques are emphasized herein, it will be appreciated that analogue and mixed analogue-digital techniques are well known for detecting various waveform characteristics such as those described herein, and may also be used as desired.

The techniques described herein are also useful in systems having multi-electrode leads. In one illustrative approach, each electrode on a lead may be assigned a distinct tone or note. If a particular lead has four electrodes, for example, the electrodes may be respectively represented as four notes on a scale (say F, A, C and E), and the clef (bass or treble) may be used to indicate A or V.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A method of monitoring electrical activity of the heart comprising:
   acquiring time-based data relating to electrical activity of the heart;
   identifying one or more characteristics of the data indicative of cardiac events, the cardiac events comprising atrial events and ventricular events;
   associating a first musical notation with each of the atrial events, and associating a second musical notation with each of the ventricular events, wherein the first and second musical notations are different; and
   audibly generating the musical notations to a user for every cardiac cycle.

2. The method of claim 1 further comprising:
   identifying time relationships between the identified first characteristics; and
   establishing time relationships between the musical notations associated with the identified first characteristics that are proportional to the relative time relationships between the identified first characteristics.

3. The method of claim 2 further comprising reproducing the musical notations as sound in accordance with the time relationships established between the musical notations.

4. The method of claim 1 further comprising:
   identifying second characteristics of the data indicative of relationships between cardiac events, the relationships being of different types; and
   associating a musical notation with each of the identified second characteristics in accordance with the type of relationship represented by each of the identified second characteristics.

5. The method of claim 1 further comprising:
   identifying third characteristics of the data indicative of relationships between groups of cardiac events, the relationships being of different types; and
   associating a musical notation with each of the identified third characteristics in accordance with the type of relationship represented by each of the identified third characteristics.

6. The method of claim 1 further comprising:
   identifying fourth characteristics of the data indicative of relationships between groups of cardiac events and reference groups of cardiac events, the relationships being of different types; and
   associating a musical notation with each of the identified fourth characteristics in accordance with the type of relationship represented by each of the identified fourth characteristics.

7. The method of claim 1 wherein the musical notations comprise tones of varying pitch, quality, duration, or combinations thereof.

8. The method of claim 1 wherein the musical notations comprise a series of tones.

9. The method of claim 1 wherein the musical notations comprise sound stylized with staccato, crescendo, or slur.

10. A method of monitoring electrical activity of the heart comprising:
    acquiring a waveform of electrical activity of the heart;
    generating cardiac markers for characteristics of the waveform indicative of cardiac events, the cardiac events comprising atrial events and ventricular events;
    linking a first musical notation to each of the cardiac markers corresponding to atrial events, and a second musical notation to each of the cardiac markers corresponding to ventricular events; and
    reproducing the musical notations as sound effectively in synchronism with the waveform for every cardiac cycle.

11. The method of claim 10 further comprising:
    acquiring atrial pacing data and ventricle pacing data;
    generating atrial pacing markers from the atrial pacing data; and
    generating ventricular pacing markers from the ventricular pacing data;
    wherein the musical notation further comprises a third tone different from the first and second tones for linking to the atrial pacing markers, and a fourth tone different from the first, second and third tones for linking to the ventricle pacing markers.

12. The method of claim 11 wherein:
    the cardiac markers comprise an atrial fibrillation marker; and
    the musical notation comprises a series of tones for linking to the atrial fibrillation marker.

13. A system for monitoring electrical activity of the heart comprising:
    means for acquiring data relating to electrical activity of the heart;
    means for identifying atrial and ventricular events within the data;
    means for associating a particular musical notation with each atrial event and a different musical notation with each ventricular event; and
    means for audibly generating the musical notations to a user for every cardiac cycle.

14. An apparatus for monitoring electrical activity of the heart comprising:
    a communications subsystem adapted to receive cardiac markers corresponding to atrial events and ventricular events in a cardiac waveform indicative of cardiac events, the cardiac markers having time relationships effectively proportional to time relationships of the atrial events and ventricular events in the cardiac waveform; and
    an audio subsystem coupled to the communications subsystem for reproducing the cardiac markers in accordance with the time relationships thereof as sound, wherein the audio subsystem generates a first musical notation for each atrial event, and a second musical notation for each ventricular event, wherein the first and second musical notations differ acoustically, and wherein the first and second musical notations are reproduced for every cardiac cycle.

15. The apparatus of claim 14 wherein the communications subsystem comprises a network interface.

16. The apparatus of claim 14 wherein the communications subsystem comprises a wireless telemetry circuit.

* * * * *